US010169696B2

United States Patent
Lee (10) Patent No.: US 10,169,696 B2
(45) Date of Patent: Jan. 1, 2019

(54) RFID SYSTEM FOR CHECKING MEDICAL ITEMS

(75) Inventor: Hui Ling Lee, Hong Kong (HK)

(73) Assignee: OSCL CORPORATION LIMITED, Hong Kong (HK)

( * ) Notice: Subject to any disclaimer, the term of this patent is extended or adjusted under 35 U.S.C. 154(b) by 952 days.

(21) Appl. No.: 13/305,731

(22) Filed: Nov. 28, 2011

(65) Prior Publication Data

US 2012/0169470 A1    Jul. 5, 2012

(30) Foreign Application Priority Data

Dec. 31, 2010 (HK) .................................. 10112305

(51) Int. Cl.
 G06K 19/077 (2006.01)
 A61B 90/90 (2016.01)

(52) U.S. Cl.
 CPC ........ G06K 19/07749 (2013.01); *A61B 90/90* (2016.02)

(58) Field of Classification Search
 CPC .................................................. H01Q 1/2216
 USPC ......................................................... 340/10.1
 See application file for complete search history.

(56) References Cited

U.S. PATENT DOCUMENTS

| 7,362,228 B2* | 4/2008 | Nycz et al. ................. 340/572.1 |
| 7,411,506 B2* | 8/2008 | Volpi ....................... G01S 13/66 340/505 |
| 8,193,938 B2* | 6/2012 | Halberthal ............. A61B 19/44 340/572.7 |
| 2002/0049650 A1* | 4/2002 | Reff ................................ 705/29 |
| 2008/0200926 A1* | 8/2008 | Verard ..................... A61B 5/06 606/130 |
| 2008/0266104 A1* | 10/2008 | Chen ................ G06K 19/07749 340/572.7 |
| 2013/0113929 A1* | 5/2013 | DeLand ....................... 348/143 |

FOREIGN PATENT DOCUMENTS

CN        101111202 A      1/2008

OTHER PUBLICATIONS

1st Office Action of counterpart Chinese Patent Application No. 201110392229.0 dated Dec. 1, 2014.

* cited by examiner

*Primary Examiner* — Vernal Brown (57) ABSTRACT

A RFID system for checking medical items includes a processing unit; two RFID readers connected with the processing unit; at least an antenna connected to each of the RFID readers; and a plurality of RFID tags being respectively attached to a plurality of medical items. The RFID tags are configured to store identification codes that respectively and uniquely correspond to the medical items that the RFID tags are attached to. The RFID readers are configured to respectively read the identification codes of the medical items from the RFID tags through the antennas before and after a surgical operation and send the identification codes to the processing unit. The processing unit is configured to receive the identification codes and determine the completeness of the medical items based on the received identification codes. A method for checking medical items with the RFID system is also provided.

12 Claims, 6 Drawing Sheets

RFID SYSTEM FOR CHECKING MEDICAL ITEMS

CROSS REFERENCE TO RELATED PATENT APPLICATION

The present patent application claims priority of Hong Kong short term patent application No. 10112305.3, filed on Dec. 31, 2010, the entire content of which is hereby incorporated by reference.

FIELD OF THE PATENT APPLICATION

The present patent application relates to RFID (Radio Frequency Identification) technologies and more particularly to a RFID system for checking medical items and a method for checking medical items with the RFID system.

BACKGROUND

In the preparation process for a surgical operation in a medical institution such as a hospital, medical items that are used in the operation need to be checked accurately. These medical items include medical instruments such as hemostats and scalpels, and medical consumables such as gauze and tampons. Currently, such checking procedures are manually carried out by medical staff. If a particular medical instrument or consumable is found missing or not correctly disposed in the middle of the surgical operation, which may have been caused by human errors during the above preparation process, precious time will be lost in the operation and the result of the operation may be adversely affected.

SUMMARY

The present patent application is directed to a RFID system for checking medical items. In one aspect, the RFID system includes a processing unit; two RFID readers connected with the processing unit; at least an antenna connected to each one of the RFID readers; and a plurality of RFID tags being respectively attached to a plurality of medical items. The RFID tags include a first group of RFID tags attached to the medical items before a surgical operation and a second group of RFID tags attached to the medical items after the surgical operation. The RFID tags are configured to store identification codes that respectively and uniquely correspond to the medical items that the RFID tags are attached to. The RFID readers are configured to read the identification codes of the medical items from the RFID tags through the antenna and send the identification codes to the processing unit. One of the RFID readers is configured to read the first group of RFID tags through one antenna that is connected to the RFID reader. The other one of the RFID readers is configured to read the second group of RFID tags through another antenna that is connected to the other RFID reader. The processing unit is configured to receive the identification codes and determine the completeness of the medical items based on the received identification codes. The processing unit is further configured to store a predetermined standard list of required medical items and determine the completeness of the medical items based on whether the medical items corresponding to the identification codes are identical with the medical items on the standard list.

The at least one antenna may be embedded in each of the RFID readers.

If the processing unit determines the medical items are complete, the processing unit may be configured to generate an indication of completeness; if the processing unit determines the medical items are not complete, the processing unit may be configured to generate a list of missing medical items and a warning.

The RFID system may further include a first tray and a second tray. The first tray is configured to load medical items before the surgical operation. The second tray is configured to load medical items after the surgical operation. The antennas being connected to different RFID readers have coverage areas that are exclusive to each other. The first tray and the second tray are respectively disposed in mutually exclusive coverage areas of the antennas connected to different RFID readers.

One of the RFID readers may be configured to count the total numbers of the medical items in the first tray before and after the surgical operation and send the total numbers to the processing unit. The other one of the RFID readers may be configured to count the total number of the medical items in the second tray after the surgical operation and send the total number to the processing unit. The processing unit may be configured to determine whether the sum of the total numbers of the medical items in the first tray and the second tray after the operation is equal to the total number of medical items in the first tray before the operation.

Two antennas may be connected to each RFID reader.

In another aspect, the present patent application provides a method for checking medical items. The method includes: before a surgical operation, reading identification codes of a plurality of medical items disposed in a first tray from a first plurality of RFID tags respectively attached to the medical items through at least a first antenna and sending the identification codes to a processing unit with a first RFID reader; and receiving the identification codes and determining whether the medical items disposed in the first tray are complete according to the received identification codes with the processing unit; and after the operation, reading identification codes of a plurality of medical items disposed in the second tray from a second plurality of RFID tags respectively attached to the medical items through at least a second antenna and sending the identification codes to the processing unit with a second RFID reader; and receiving the identification codes and determining whether the medical items disposed in the second tray are complete according to the received identification codes with the processing unit.

The step of determining whether the medical items disposed in the first tray are complete before the surgical operation may include determining whether the medical items corresponding to the received identification codes are identical with the medical items on a first predetermined standard list stored in the processing unit.

The step of determining whether the medical items disposed in the second tray are complete after the surgical operation may include determining whether the medical items corresponding to the received identification codes are identical with the medical items on a second predetermined standard list stored in the processing unit.

The method may further include counting the total number of the medical items in the first tray and sending the total number to the processing unit with the first RFID reader before the surgical operation, counting the total number of the medical items in the second tray and sending the total number to the processing unit with the second RFID reader after the surgical operation, and counting the total number of the medical items in the first tray and sending the total number to the processing unit with the first RFID reader after the surgical operation.

The method may further include determining whether the sum of the total numbers of the medical items in the first tray and the second tray after the operation is equal to the total number of medical items in the first tray before the operation with the processing unit.

The method may further include generating an indication of completeness with the processing unit after determining that the medical items disposed in the first tray and the second tray are complete and determining that the sum of the total numbers of the medical items in the first tray and the second tray after the operation is equal to the total number of medical items in the first tray before the operation; and generating a list of missing medical items and a warning after determining that the medical items disposed in the first tray or the second tray are not complete or after determining that the sum of the total numbers of the medical items in the first tray and the second tray after the operation is not equal to the total number of medical items in the first tray before the operation.

The method may further include disposing the first tray in the reading range of the first RFID reader and disposing the second tray in the reading range of the second RFID reader, the reading range of the first RFID reader being exclusive to the reading range of the second RFID reader.

In the step of reading identification codes of the plurality of medical items disposed in the first tray from a first plurality of RFID tags respectively attached to the medical items, the identification codes may be read through two antennas, and in the step of reading identification codes of the plurality of medical items disposed in the second tray from a second plurality of RFID tags respectively attached to the medical items, the identification codes may be read through another two antennas.

In yet another aspect, the present patent application provides a RFID system for checking medical items. The RFID system includes: a processing unit; two RFID readers connected with the processing unit; at least an antenna connected to each of the RFID readers; and a plurality of RFID tags being respectively attached to a plurality of medical items. The RFID tags are configured to store identification codes that respectively and uniquely correspond to the medical items that the RFID tags are attached to. The RFID readers are configured to respectively read the identification codes of the medical items from the RFID tags through the antennas before and after a surgical operation and send the identification codes to the processing unit. The processing unit is configured to receive the identification codes and determine the completeness of the medical items based on the received identification codes.

The processing unit may be further configured to store a predetermined standard list of required medical items and determine the completeness of the medical items based on whether the medical items corresponding to the identification codes are identical with the medical items on the standard list.

If the processing unit determines the medical items are complete, the processing unit may be configured to generate an indication of completeness. If the processing unit determines the medical items are not complete, the processing unit may be configured to generate a list of missing medical items and a warning.

The RFID system may further include a first tray and a second tray. The first tray is configured to load medical items before the surgical operation. The second tray is configured to load medical items after the surgical operation. The antennas being connected to different RFID readers have coverage areas that are exclusive to each other. The first tray and the second tray are respectively disposed in mutually exclusive coverage areas of the antennas connected to different RFID readers.

One of the RFID readers may be configured to count the total numbers of the medical items in the first tray before and after the surgical operation and send the total numbers to the processing unit. The other one of the RFID readers may be configured to count the total number of the medical items in the second tray after the surgical operation and send the total number to the processing unit. The processing unit may be configured to determine whether the sum of the total numbers of the medical items in the first tray and the second tray after the operation is equal to the total number of medical items in the first tray before the operation.

Two antennas may be connected to each of the RFID readers.

DETAILED DESCRIPTION

Reference will now be made in detail to a preferred embodiment of the RFID system for checking medical items disclosed in the present patent application, examples of which are also provided in the following description. Exemplary embodiments of the RFID system for checking medical items disclosed in the present patent application are described in detail, although it will be apparent to those skilled in the relevant art that some features that are not particularly important to an understanding of the RFID system for checking medical items may not be shown for the sake of clarity.

Furthermore, it should be understood that the RFID system for checking medical items disclosed in the present patent application is not limited to the precise embodiments described below and that various changes and modifications thereof may be effected by one skilled in the art without departing from the spirit or scope of the protection. For example, elements and/or features of different illustrative embodiments may be combined with each other and/or substituted for each other within the scope of this disclosure.

Figure 1:
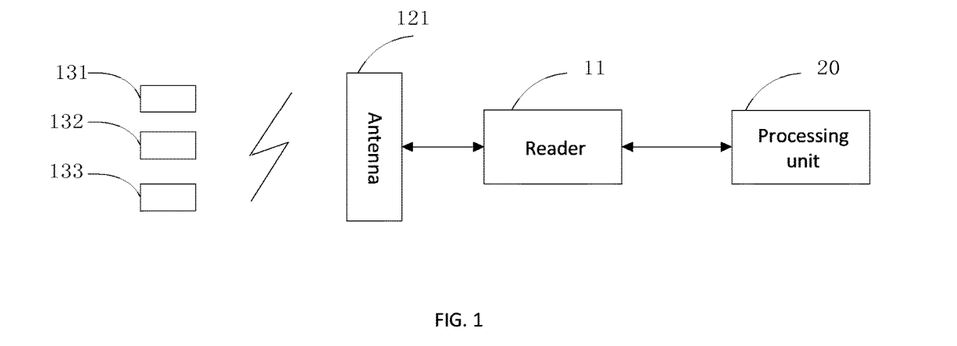
FIG. 1 is a block diagram of a RFID system for checking medical items according to an embodiment of the present patent application.

FIG. 1 is a block diagram of a RFID system for checking medical items according to an embodiment of the present patent application. Referring to FIG. 1, the RFID system includes a processing unit or processor 20, a RFID reader 11, an antenna 121 and three RFID tags 131, 132 and 133, which are attached to three medical items (not shown in FIG. 1) respectively. The RFID reader 11 is connected with the processing unit 20. The processing unit 20 may be a remote computer or remote server. The antenna 121 is connected with the RFID reader 11. The RFID tags 131, 132 and 133 are configured to store identification codes that correspond to the medical items that the RFID tags 131, 132 and 133 are attached to. The identification codes are the codes that respectively and uniquely correspond to the medical items and can be used to identify the individual medical items. The medical items may be surgical instruments hemostats and scalpels and/or surgical consumables such as gauze and tampons. The RFID reader 11 is configured to read the identification codes of the medical items from the RFID tags 131, 132 and 133 through the antenna 121 and send the identification codes to the processing unit 20. The processing unit 20 is configured to receive the identification codes and determine the completeness of the medical items based on the received identification codes.

It is understood that the number of the medical items and the corresponding RFID tags is not limited to three, and may be determined by the actual requirements in the surgical operation. In addition, the antenna 121 may be externally connected to the RFID reader 11, or alternatively embedded in the RFID reader 11.

In this embodiment, the processing unit 20 is configured to store a predetermined standard list of all the medical items that are actually required by the surgical operation beforehand. After receiving the identification codes of the medical items, the processing unit 20 is configured to determine whether the medical items corresponding to the identification codes are identical with the medical items on the standard list. If yes, the processing unit is configured to indicate that the medical items are complete and correctly processed. If not, the processing unit is configured to generate a list of missing medical items and a warning so as to give the medical staff a notice.

Figure 2:
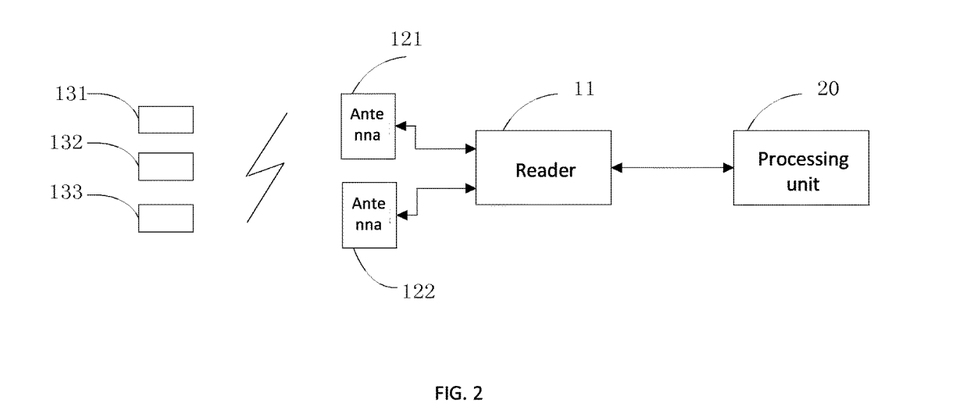
FIG. 2 is a block diagram of a RFID system for checking medical items according to another embodiment of the present patent application.

FIG. 2 is a block diagram of a RFID system for checking medical items according to another embodiment of the present patent application. Referring to FIG. 2, the RFID system includes a processing unit 20, a RFID reader 11, a first antenna 121, a second antenna and three RFID tags 131, 132 and 133, which are attached to three medical items (not shown in FIG. 1) respectively. The RFID reader 11 is connected with the processing unit 20. The processing unit 20 may be a remote computer or remote server. The antenna 121 and the antenna 122 are both connected with the RFID reader 11. The antennas 121 and 122 may be externally connected to the RFID reader 11, or alternatively embedded in the RFID reader 11. This embodiment is similar to the previous embodiment except that there are two antennas instead of one. The coverage area of the two antennas 121 and 122 is greater than the coverage area of only one antenna. It is understood that the number of antennas is not limited to two and may be three, four, and etc.

Figure 3:
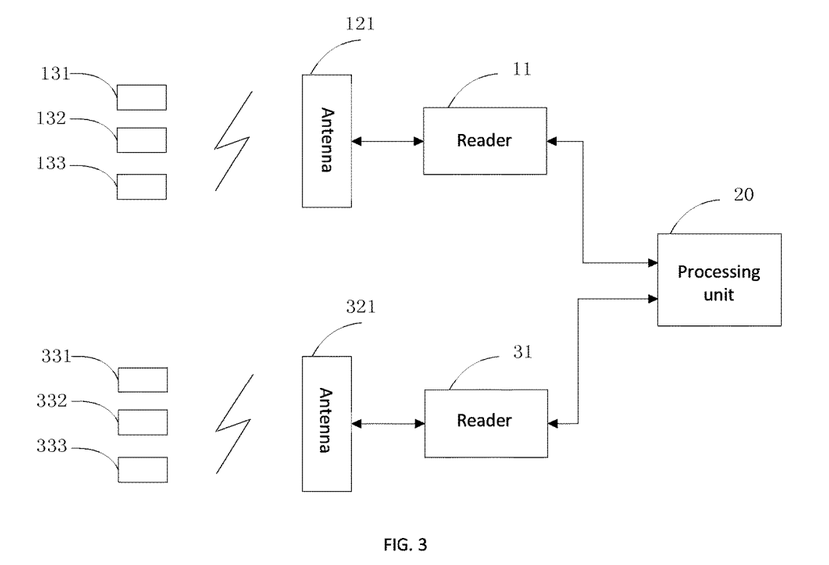
FIG. 3 is a block diagram of a RFID system for checking medical items according to yet another embodiment of the present patent application.

FIG. 3 is a block diagram of a RFID system for checking medical items according to yet another embodiment of the present patent application. Referring to FIG. 3, the RFID system is configured to check the completeness of a plurality of medical items before and after a surgical operation. The medical items include surgical instruments and/or surgical consumables. The RFID system includes a processing unit 20, a first RFID reader 11, a second RFID reader 31, a first antenna 121, a second antenna 321, three RFID tags 131, 132 and 133 that are respectively attached to three medical items (not shown in FIG. 3) before a surgical operation, and three RFID tags 331, 332 and 333 that are respectively attached to three medical items (not shown in FIG. 3) after the surgical operation. The first RFID reader 11 and the second RFID reader 31 are respectively connected with the processing unit 20. The first antenna 121 is connected with the first RFID reader 11. The second antenna 321 is connected with the second RFID reader 31. The RFID tags 131, 132 133, 331, 332 and 333 are configured to store identification codes corresponding to the medical items that the RFID tags are attached to respectively. The medical items before the surgical operation are disposed in the coverage area of the first antenna 121 (i.e. the reading range of the first RFID reader 11), for example in a first tray in that area. The medical items after the surgical operation are disposed in the coverage area of the second antenna 321 (i.e. the reading range of the second RFID reader 31), for example in a second tray in that area. The coverage area of the first antenna 121 is exclusive of the coverage area of the second antenna 321. As a result, the first RFID reader 11 can only read the RFID tags 131, 132 and 133, which are attached to the medical items before the surgical operation, and the second RFID reader 31 can only read RFID tags 331, 332 and 333, which are attached to the medical items after the surgical operation. It is understood that in this embodiment the number of trays is not limited to two.

Before the surgical operation, the first RFID reader 11 is configured to read the identification codes of the medical items in the first tray through the first antenna 121, and send the identification codes to the processing unit 20. Based on the received identification codes, the processing unit 20 is configured to determine whether the medical items in the first tray are complete. During the process of the operation, the medical items originally disposed in the first tray are gradually moved to the second tray. After the operation is completed, the second RFID reader 31 is configured to read the identification codes of the medical items in the second tray through the second antenna 321, and send the identification codes to the processing unit 20. Based on the received identification codes, the processing unit 20 is configured to determine whether the medical items in the second tray are complete.

The processing unit 20 is configured to determine whether the medical items, before and after the operation, are complete in the following way. The processing unit 20 is configured to store a first standard list of the medical items before the surgical operation and a second standard list of medical items after the surgical operation. Before the operation, the processing unit 20 is configured to determine whether the medical items corresponding to the identification codes are identical with the medical items on the first standard list. If not, a list of missing medical items and a warning will be generated so as to give the medical staff a notice. After the operation, the processing unit 20 is configured to determine whether the medical items corresponding to the identification codes are identical with the medical items on the second standard list. If not, a list of missing medical items and a warning will be generated so as to give the medical staff a notice.

Preferably, the first RFID reader 11 is configured to count the total numbers of the medical items in the first tray before and after the operation and sending the total numbers to the processing unit 20. The second RFID reader 31 configured to count the total number of the medical items in the second tray after the operation and sending the total number to the processing unit 20. The processing unit 20 is configured to determine whether the sum of the total numbers of the medical items in the first tray and the second tray after the operation is equal to the total number of medical items in the first tray before the operation. If not, a list of missing medical items and a warning will be generated by the processing unit 20 so as to give the medical staff a notice.

Figure 4:
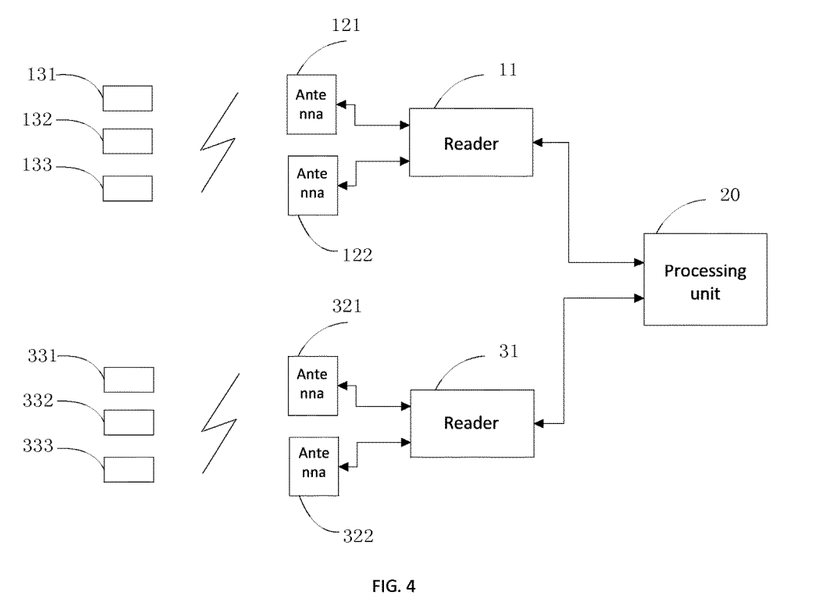
FIG. 4 is a block diagram of a RFID system for checking medical items according to still another embodiment of the present patent application.

FIG. 4 is a block diagram of a RFID system for checking medical items according to still another embodiment of the present patent application. The RFID system in this embodiment is similar to the RFID system in the embodiment illustrated in FIG. 3 except that each RFID reader is connected with two antennas. More specifically, the first RFID reader 11 is connected with the antenna 121 and the antenna 122. The second RFID reader 31 is connected with the antenna 321 and the antenna 322. It is understood that with such architecture more than two antennas may be connected to each RFID reader.

Figure 5:
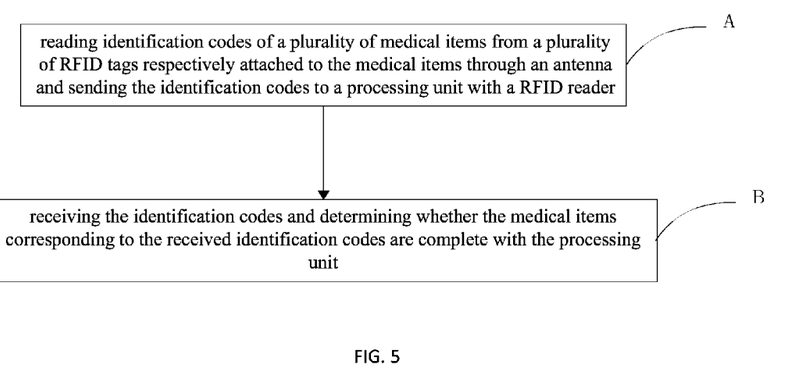
FIG. 5 is a flow chart illustrating a method for checking medical items according to still another embodiment of the present patent application.

FIG. 5 is a flow chart illustrating a method for checking medical items according to still another embodiment of the present patent application. Referring to FIG. 1 and FIG. 5, the method includes:
A) reading identification codes of a plurality of medical items from a plurality of RFID tags respectively attached to the medical items through an antenna and sending the identification codes to a processing unit with a RFID reader; and
B) receiving the identification codes and determining whether the medical items corresponding to the received identification codes are complete with the processing unit.

Figure 6:
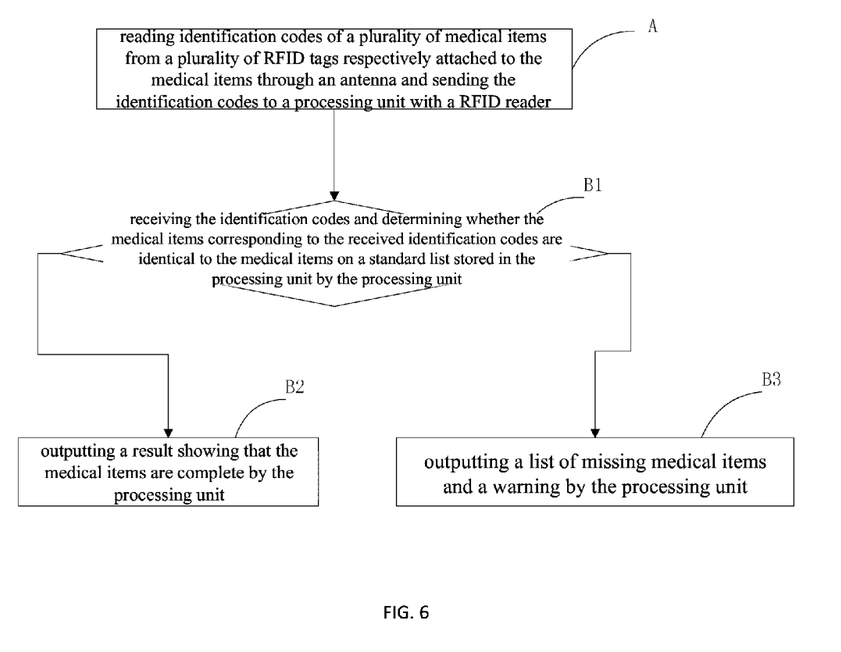
FIG. 6 is a flow chart illustrating a method for checking medical items according to still another embodiment of the present patent application.

FIG. 6 is a flow chart illustrating a method for checking medical items according to still another embodiment of the present patent application. Referring to FIG. 6, the method includes the steps of:
A) reading identification codes of a plurality of medical items from a plurality of RFID tags respectively attached to the medical items through an antenna and sending the identification codes to a processing unit with a RFID reader;
B1) receiving the identification codes and determining whether the medical items corresponding to the received identification codes are identical with the medical items on a standard list stored in the processing unit by the processing unit; if yes, executing the step B2; if no, executing the step B3;
B2) outputting a result showing that the medical items are complete by the processing unit; and
B3) outputting a list of missing medical items and a warning with the processing unit.

Figure 7A:
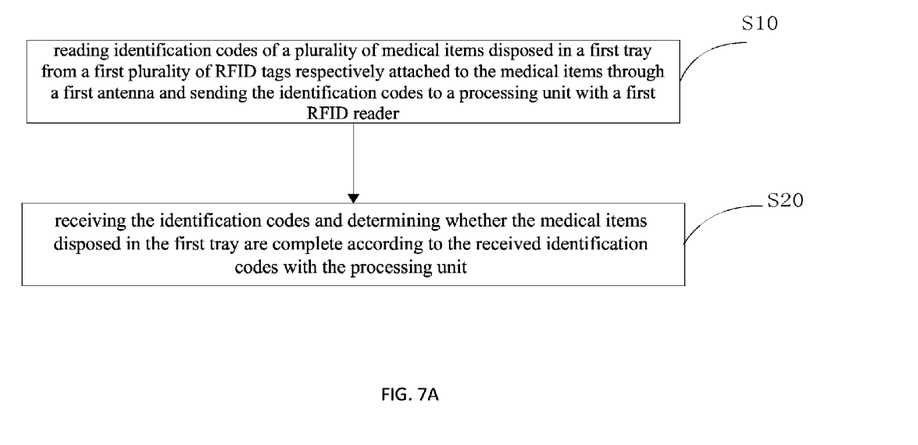
FIG. 7A is a flow chart illustrating a method for checking medical items before a surgical operation according to still another embodiment of the present patent application.
Figure 7B:
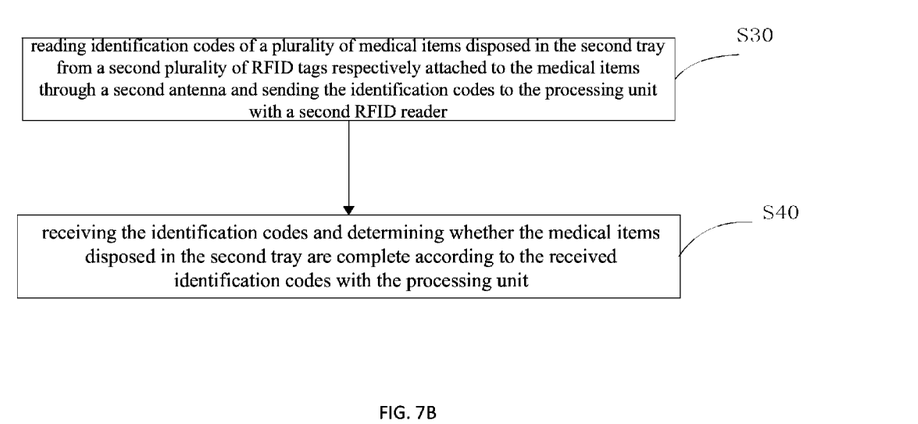
FIG. 7B is a flow chart illustrating a method for checking medical items after a surgical operation according to the embodiment illustrated by FIG. 7A.

FIG. 7A is a flow chart illustrating a method for checking medical items before a surgical operation according to still another embodiment of the present patent application. FIG. 7B is a flow chart illustrating a method for checking medical items after a surgical operation according to the embodiment illustrated by FIG. 7A. Referring to FIG. 7A, FIG. 7B and FIG. 3, the method for checking the completeness of medical items before and after a surgical operation includes:
before the operation, executing the following steps:
S10: reading identification codes of a plurality of medical items disposed in a first tray from a first plurality of RFID tags respectively attached to the medical items through a first antenna and sending the identification codes to a processing unit with a first RFID reader;
S20: receiving the identification codes and determining whether the medical items disposed in the first tray are complete according to the received identification codes with the processing unit;
after the operation, executing the following steps:
S30: reading identification codes of a plurality of medical items disposed in the second tray from a second plurality of RFID tags respectively attached to the medical items through a second antenna and sending the identification codes to the processing unit with a second RFID reader;
S40: receiving the identification codes and determining whether the medical items disposed in the second tray are complete according to the received identification codes with the processing unit.

Figure 8A:
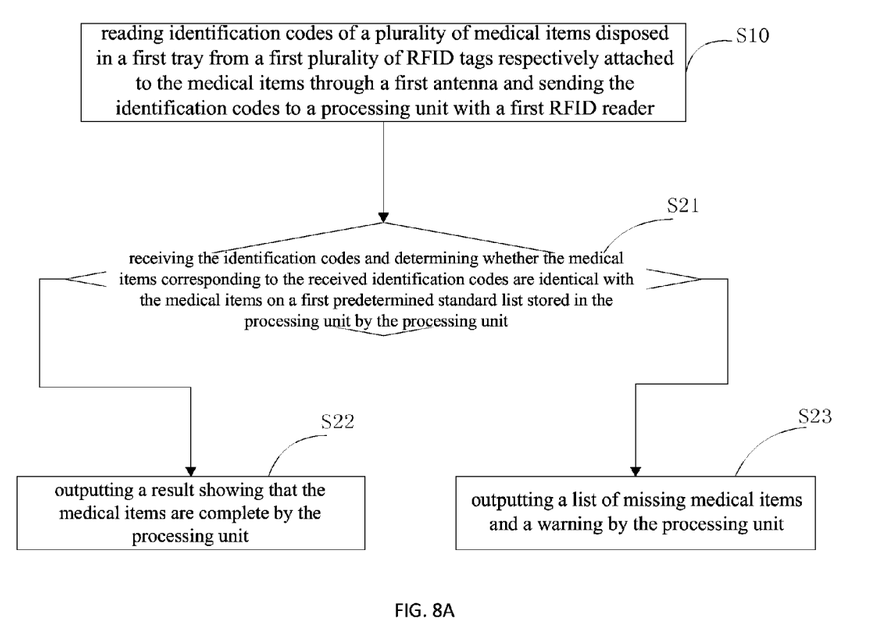
FIG. 8A is a flow chart illustrating a method for checking medical items before a surgical operation according to still another embodiment of the present patent application.
Figure 8B:
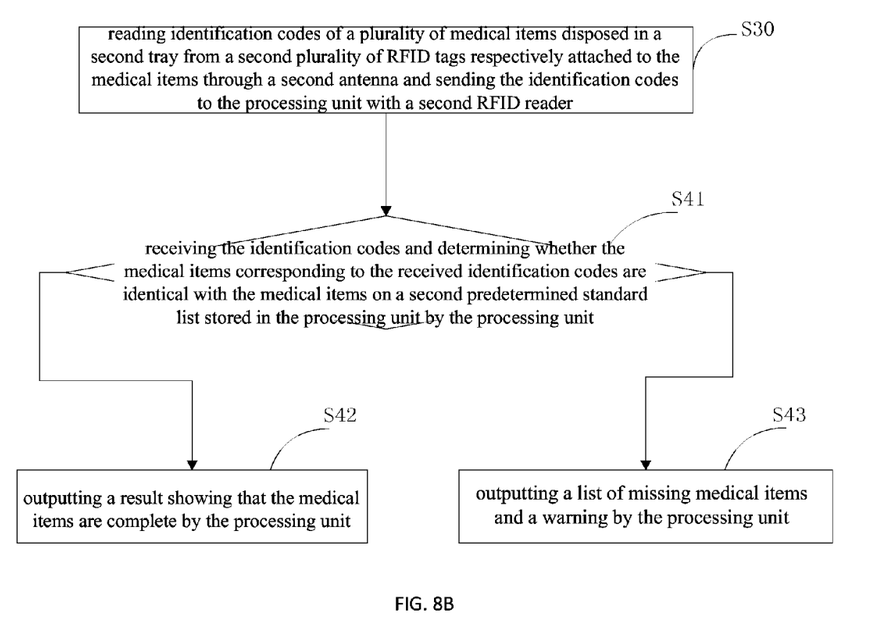
FIG. 8B is a flow chart illustrating a method for checking medical items after a surgical operation according to the embodiment illustrated by FIG. 8A.

FIG. 8A is a flow chart illustrating a method for checking medical items before a surgical operation according to still another embodiment of the present patent application. FIG. 8B is a flow chart illustrating a method for checking medical items after a surgical operation according to the embodiment illustrated by FIG. 8A. Referring to FIG. 8A and FIG. 8B, the method for checking the completeness of medical items before and after a surgical operation includes:
before the operation, executing the following steps:
S10: reading identification codes of a plurality of medical items disposed in a first tray from a first plurality of RFID tags respectively attached to the medical items through a first antenna and sending the identification codes to a processing unit with a first RFID reader;
S21: receiving the identification codes and determining whether the medical items corresponding to the received identification codes are identical with the medical items on a first predetermined standard list stored in the processing unit by the processing unit; if yes, executing the step S22; if no, executing the step S23;
S22: outputting a result showing that the medical items are complete by the processing unit; and
S23: outputting a list of missing medical items and a warning with the processing unit.
after the operation, executing the following steps:
S30: reading identification codes of a plurality of medical items disposed in a second tray from a second plurality of RFID tags respectively attached to the medical items through a second antenna and sending the identification codes to the processing unit with a second RFID reader;
S41: receiving the identification codes and determining whether the medical items corresponding to the received identification codes are identical with the medical items on a second predetermined standard list stored in the processing unit by the processing unit; if yes, executing the step S42; if no, executing the step S43;
S42: outputting a result showing that the medical items are complete with the processing unit; and
S43: outputting a list of missing medical items and a warning with the processing unit.

Figure 9A:
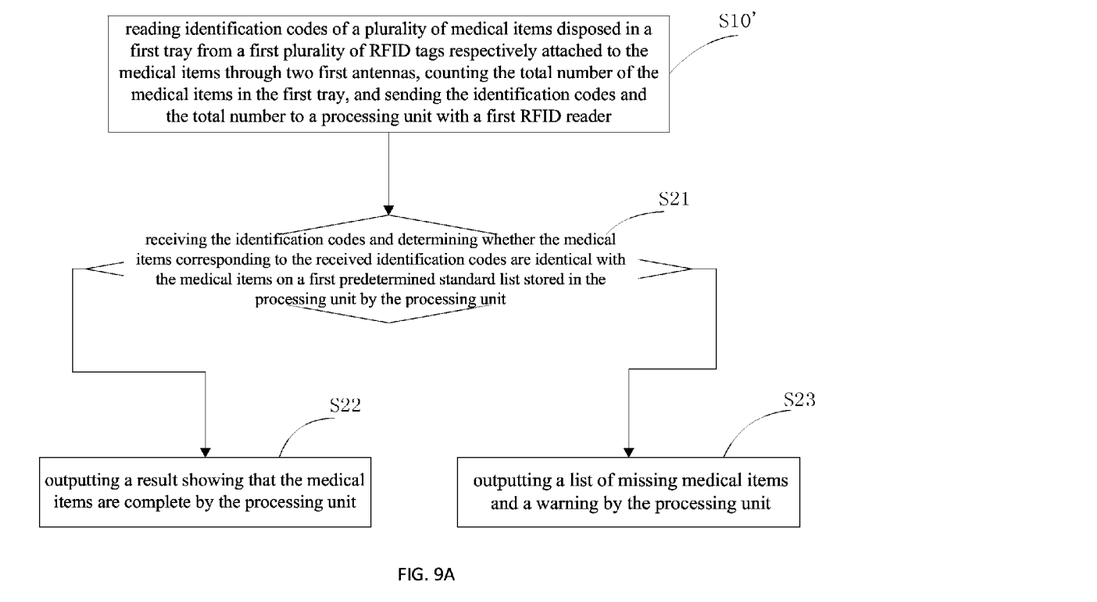
FIG. 9A is a flow chart illustrating a method for checking medical items before a surgical operation according to still another embodiment of the present patent application.
Figure 9B:
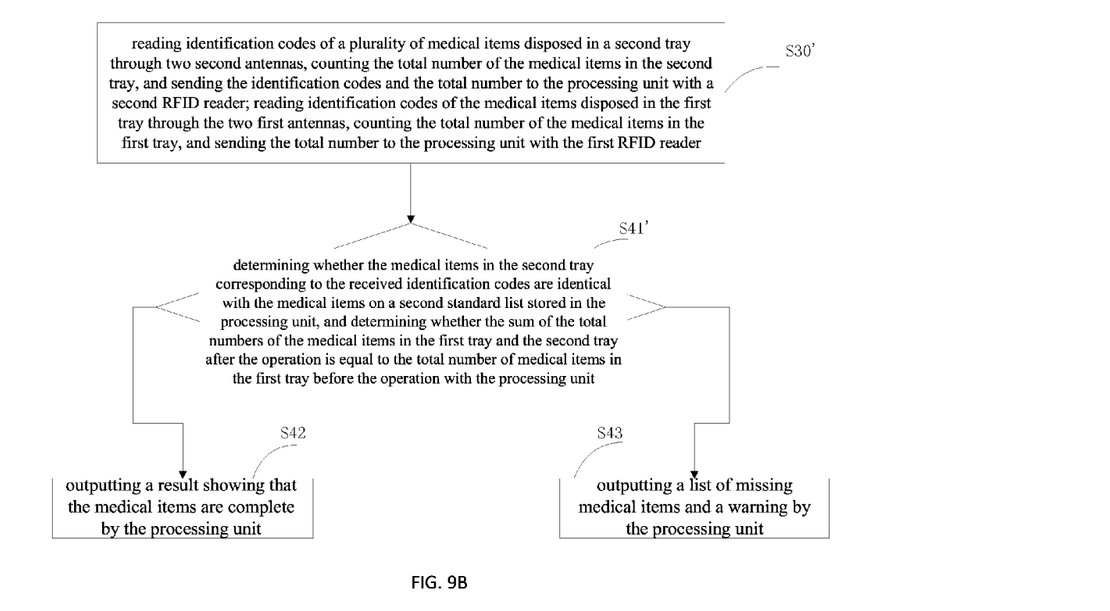
FIG. 9B is a flow chart illustrating a method for checking medical items after a surgical operation according to the embodiment illustrated by FIG. 9A.

FIG. 9A is a flow chart illustrating a method for checking medical items before a surgical operation according to still another embodiment of the present patent application. FIG. 9B is a flow chart illustrating a method for checking medical items after a surgical operation according to the embodiment illustrated by FIG. 9A. The method for checking the completeness of medical items before and after a surgical operation in this embodiment includes the steps S21, S22, S23, S42 and S43 in the embodiment illustrated in FIG. 8A and FIG. 8B, and the method further includes:

before the operation:

S10': reading identification codes of a plurality of medical items disposed in a first tray from a first plurality of RFID tags respectively attached to the medical items through two first antennas, counting the total number of the medical items in the first tray, and sending the identification codes and the total number to a processing unit with a first RFID reader;

after the operation:

S30': reading identification codes of a plurality of medical items disposed in a second tray from a second plurality of RFID tags respectively attached to the medical items through two second antennas, counting the total number of the medical items in the second tray, and sending the identification codes and the total number to the processing unit with a second RFID reader; reading identification codes of the medical items disposed in the first tray from the first plurality of RFID tags respectively attached to the medical items through the two first antennas, counting the total number of the medical items in the first tray, and sending the total number to the processing unit with the first RFID reader;

S41': receiving the identification codes and the total number of the medical items in the second tray, and the total number of the medical items in the first tray, determining whether the medical items in the second tray corresponding to the received identification codes are identical with the medical items on a second standard list stored in the processing unit, and determining whether the sum of the total numbers of the medical items in the first tray and the second tray after the operation is equal to the total number of medical items in the first tray before the operation with the processing unit; if yes, executing the step S42; if no, executing the step S43.

It is understood that in this embodiment, the step S10' substitutes the step S10 in the embodiment illustrated by FIG. 8A and FIG. 8B; the step S30' substitutes the step S30 in the embodiment illustrated by FIG. 8A and FIG. 8B; the step S41' substitutes the step S41 in the embodiment illustrated by FIG. 8A and FIG. 8B. The steps S21, S22, S23, S42 and S43 in this embodiment are the same as in the embodiment illustrated by FIG. 8A and FIG. 8B.

While the present patent application has been shown and described with particular references to a number of embodiments thereof, it should be noted that various other changes or modifications may be made without departing from the scope of the present invention.

What is claimed is:

1. A RFID system for checking medical items comprising:
   a processor;
   a first RFID reader connected with the processor;
   a second RFID reader connected with the processor;
   a first antenna connected to the first RFID reader and covering a first coverage area;
   a second antenna connected to the second RFID reader and covering a second coverage area;
   a first tray disposed in the first coverage area;
   a second tray disposed in the second coverage area; and
   a plurality of RFID tags being respectively attached to a plurality of medical items;
   wherein the RFID tags are configured to store identification codes that respectively and uniquely correspond to the medical items that the RFID tags are attached to;
   the first RFID reader only reads the identification codes of the medical items from the RFID tags through the first antenna and send the identification codes to the processor before a surgical operation, the second RFID reader only reads the identification codes of the medical items from the RFID tags through the second antenna and send the identification codes to the processor after the surgical operation;
   the first tray is adapted to load the medical items before the surgical operation, the second tray is adapted to load at least one of the medical items moved from the first tray during the surgical operation;
   the first coverage area and the second coverage area are mutually exclusive;
   wherein the processor stores a first predetermined standard list of the medical items to be loaded in the first tray before the surgical operation, and a second predetermined standard list of the at least one of the medical items to be loaded in the second tray during the operation, and wherein the processor generates a list of missing medical items and a warning after determining that a sum of total numbers of the medical items in the first tray and the second tray after the operation are not identical with a total number of the medical items in the first tray before the operation; and
   wherein the first and second trays are open trays.

2. The RFID system of claim 1, wherein the first antenna is embedded in the first RFID reader and the second antenna is embedded in the second RFID reader.

3. The RFID system of claim 1, wherein the processor generates a first list of missing medical items and a first warning after determining that the medical items corresponding to the identification codes read in the first tray are not identical with medical items on a first standard list before the operation; and
   the processor generates a second list of missing medical items and a second warning after determining that the medical items corresponding to the identification codes read in the second tray are not identical with medical items on a second standard list after the operation.

4. A method for checking medical items comprising:
   before a surgical operation, reading identification codes of a plurality of medical items disposed in a first tray from a first plurality of RFID tags respectively attached to the medical items through at least a first antenna and sending the identification codes to a processor with a first RFID reader; and receiving the identification codes and determining whether the medical items disposed in the first tray are complete according to the received identification codes with the processor; and
   after the operation, reading identification codes of at least one of the medical items disposed in a second tray from a second plurality of RFID tags respectively attached to the at least one of the medical items through at least a second antenna and sending the identification codes to the processor with a second RFID reader; and receiving the identification codes and determining whether the medical items disposed in the second tray are complete according to the received identification codes with the processor, and wherein the processor generates a list of missing medical items and a warning after determining that a sum of total numbers of the medical items in the first tray and the second tray after the operation are not identical with a total number of the medical items in the first tray before the operation;

wherein the first antenna covers a first coverage area and the first tray is disposed in the first coverage area; the second antenna covers a second coverage area and the second tray is disposed in the second coverage area; and the first coverage area and the second coverage area are mutually exclusive;

wherein the first and second trays are open trays.

5. The method of claim 4, wherein the step of determining whether the medical items disposed in the first tray are complete before the surgical operation comprises determining whether the medical items corresponding to the received identification codes are identical with the medical items on a first predetermined standard list predetermined and stored in the processor.

6. The method of claim 4, wherein the step of determining whether the medical items disposed in the second tray are complete after the surgical operation comprises determining whether the medical items corresponding to the received identification codes are identical with the medical items on a second predetermined standard list predetermined and stored in the processor.

7. The method of claim 4 further comprising counting the total number of the medical items in the first tray and sending the total number to the processor with the first RFID reader before the surgical operation, counting the total number of the medical items in the second tray and sending the total number to the processor with the second RFID reader after the surgical operation, and counting the total number of the medical items in the first tray and sending the total number to the processor with the first RFID reader after the surgical operation.

8. The method of claim 7 further comprising determining whether the sum of the total numbers of the medical items in the first tray and the second tray after the operation is equal to the total number of medical items in the first tray before the operation with the processor.

9. The method of claim 8 further comprising
generating an indication of completeness with the processor after determining that the medical items disposed in the first tray and the second tray are complete and determining that the sum of the total numbers of the medical items in the first tray and the second tray after the operation is equal to the total number of medical items in the first tray before the operation; and generating a list of missing medical items and a warning after determining that the medical items disposed in the first tray or the second tray are not complete or after determining that the sum of the total numbers of the medical items in the first tray and the second tray after the operation is not equal to the total number of medical items in the first tray before the operation.

10. The method of claim 4, wherein in the step of reading identification codes of the plurality of medical items disposed in the first tray from a first plurality of RFID tags respectively attached to the medical items, the identification codes are read through two antennas, and in the step of reading identification codes of the plurality of medical items disposed in the second tray from a second plurality of RFID tags respectively attached to the medical items, the identification codes are read through another two antennas.

11. The method of claim 4, further comprising:

generating a first list of missing medical items and a first warning after determining that the medical items corresponding to the identification codes read in the first tray are not identical with medical items on a first standard list before the operation; and generating a second list of missing medical items and a second warning after determining that the medical items corresponding to the identification codes read in the second tray are not identical with medical items on a second standard list after the operation.

12. The method of claim 11, further comprising:

counting total numbers of the medical items in the first tray before and after the operation;

counting a total number of the medical items in the second tray after the operation; and generating a list of missing medical items and a warning after determining that a sum of the total numbers of the medical items in the first tray and the second tray after the operation are not identical with the total number of the medical items in the first tray before the operation.

* * * * *